(12) United States Patent
Djupesland et al.

(10) Patent No.: US 10,076,614 B2
(45) Date of Patent: Sep. 18, 2018

(54) NASAL DELIVERY DEVICES (71) Applicant: OPTINOSE AS, Oslo (NO)

(72) Inventors: Per Gisle Djupesland, Oslo (NO);
Joseph Gordon, Mansfield, MA (US);
Michael Leclerc, Cranston, RI (US);
Ramy A Mahmoud, Skillman, NJ (US); Shane Siwinski, Providence, RI (US)

(73) Assignee: OptiNose AS, Oslo (NO)

( * ) Notice: Subject to any disclaimer, the term of this patent is extended or adjusted under 35 U.S.C. 154(b) by 602 days.

(21) Appl. No.: 14/380,801

(22) PCT Filed: Feb. 25, 2013

(86) PCT No.: PCT/EP2013/053747
§ 371 (c)(1),
(2) Date: Aug. 25, 2014

(87) PCT Pub. No.: WO2013/124492
PCT Pub. Date: Aug. 29, 2013

(65) Prior Publication Data
US 2015/0013677 A1    Jan. 15, 2015

Related U.S. Application Data (60) Provisional application No. 61/603,093, filed on Feb. 24, 2012.

(51) Int. Cl.
*A61M 15/08* (2006.01)
*A61M 15/00* (2006.01)

(52) U.S. Cl.
CPC ........ *A61M 15/08* (2013.01); *A61M 15/0021* (2014.02); *A61M 15/0098* (2014.02);
(Continued)

(58) Field of Classification Search
CPC .............. A61M 15/08; A61M 15/0021; A61M 15/0098; A61M 2210/0625;
(Continued)

(56) References Cited

U.S. PATENT DOCUMENTS

| 369,849 | A | * | 9/1887 | Werner | ................. A61M 15/08 128/203.22 |
| 605,436 | A | | 6/1898 | Kellogg | |

(Continued)

FOREIGN PATENT DOCUMENTS

| CN | A-1258223 | 6/2010 |
| GB | 2405350 | 3/2005 |

(Continued)

OTHER PUBLICATIONS

Cindy H. Dubin, *Nothing to Sneeze At*, Pharmaceutical Formulation & Quality Magazine (Jan. 29, 2003).

(Continued)

*Primary Examiner* — Kathryn E Ditmer
(74) *Attorney, Agent, or Firm* — Finnegan, Henderson, Farabow, Garrett & Dunner, LLP (57) ABSTRACT A nasal delivery device for delivering substance to a nasal cavity of a subject comprises: a housing (15); a nosepiece (17) for fitting to a nasal cavity of the subject; a mouthpiece (19) through which the subject in use exhales; and a flexible coupling (20) which couples the mouthpiece to the housing, wherein the flexible coupling provides for asymmetric translation of the mouthpiece relative to the nosepiece.

47 Claims, 7 Drawing Sheets (52) U.S. Cl.
CPC ............... *A61M 2202/064* (2013.01); *A61M 2205/0216* (2013.01); *A61M 2210/0618* (2013.01); *A61M 2210/0625* (2013.01)

(58) Field of Classification Search
CPC .. A61M 2210/0618; A61M 2205/0216; A61M 2202/064
USPC .................................................. 128/203.18
See application file for complete search history.

(56) References Cited

U.S. PATENT DOCUMENTS

| | | | |
|---|---|---|---|
| 642,748 A | 2/1900 | Manners | |
| 658,436 A * | 9/1900 | Groth .................... | A61M 15/08 128/203.18 |
| 746,749 A * | 12/1903 | Seidel .................... | A61M 15/08 128/203.18 |
| 794,641 A * | 7/1905 | Ramey ................... | A61M 15/08 128/203.18 |
| 902,832 A * | 11/1908 | Philbrook ............. | A61M 15/08 128/203.18 |
| 2,470,297 A * | 5/1949 | Fields .................... | A61M 15/00 128/203.15 |
| 4,270,778 A * | 6/1981 | Brownell ............ | A61M 16/0463 128/207.14 |
| 5,373,841 A | 12/1994 | Kyllonen | |
| 5,797,392 A | 8/1998 | Keldmann et al. | |
| 6,012,455 A * | 1/2000 | Goldstein ......... | A61M 16/0488 128/204.18 |
| 6,648,848 B1 * | 11/2003 | Keldmann ............ | A61M 15/08 604/57 |
| 6,715,485 B1 | 4/2004 | Djupesland | |
| 6,811,543 B2 * | 11/2004 | Keldmann ............ | A61M 15/08 128/203.15 |
| D530,815 S | 10/2006 | Murphy et al. | |
| 7,347,201 B2 | 3/2008 | Djupesland | |
| 7,377,901 B2 | 5/2008 | Djupesland et al. | |
| 7,481,218 B2 | 1/2009 | Djupesland | |
| 7,543,581 B2 | 6/2009 | Djupesland | |
| 7,740,014 B2 | 6/2010 | Djupesland | |
| 7,784,460 B2 | 8/2010 | Djupesland et al. | |
| 7,841,337 B2 | 11/2010 | Djupesland | |
| 7,854,227 B2 | 12/2010 | Djupesland | |
| 7,934,503 B2 | 5/2011 | Djupesland et al. | |
| 7,975,690 B2 | 6/2011 | Djupesland | |
| 8,047,202 B2 | 11/2011 | Djupesland | |
| 8,146,589 B2 | 4/2012 | Djupesland | |
| 8,171,929 B2 | 5/2012 | Djupesland et al. | |
| 8,327,844 B2 | 12/2012 | Djupesland | |
| 8,511,303 B2 | 8/2013 | Djupesland | |
| 8,522,778 B2 | 9/2013 | Djupesland | |
| 8,550,073 B2 | 10/2013 | Djupesland | |
| 8,555,877 B2 | 10/2013 | Djupesland | |
| 8,555,878 B2 | 10/2013 | Djupesland | |
| 8,590,530 B2 | 11/2013 | Djupesland et al. | |
| 8,596,278 B2 | 12/2013 | Djupesland | |
| 8,800,555 B2 | 8/2014 | Djupesland | |
| 8,875,704 B2 | 11/2014 | Djupesland et al. | |
| 8,899,229 B2 | 12/2014 | Djupesland et al. | |
| 8,910,629 B2 | 12/2014 | Djupesland et al. | |
| D723,156 S | 2/2015 | Djupesland et al. | |
| D725,769 S | 3/2015 | Djupesland et al. | |
| 8,978,647 B2 | 3/2015 | Djupesland et al. | |
| 9,010,325 B2 | 4/2015 | Djupesland et al. | |
| 9,038,630 B2 | 5/2015 | Djupesland et al. | |
| 9,067,034 B2 | 6/2015 | Djupesland et al. | |
| 9,072,857 B2 | 7/2015 | Djupesland | |
| 9,108,015 B2 | 8/2015 | Djupesland | |
| 9,119,932 B2 | 9/2015 | Djupesland | |
| 9,132,249 B2 | 9/2015 | Djupesland | |
| 9,144,652 B2 | 9/2015 | Djupesland et al. | |
| 9,168,341 B2 | 10/2015 | Djupesland | |
| 9,205,208 B2 | 12/2015 | Djupesland | |
| 9,205,209 B2 | 12/2015 | Djupesland | |
| 9,272,104 B2 | 3/2016 | Djupesland | |
| 2004/0024330 A1 | 2/2004 | Djupesland et al. | |
| 2004/0112378 A1 | 6/2004 | Djupesland | |
| 2004/0112379 A1 | 6/2004 | Djupesland | |
| 2004/0112380 A1 | 6/2004 | Djupesland | |
| 2004/0149289 A1 | 8/2004 | Djupesland | |
| 2004/0182388 A1 | 9/2004 | Djupesland | |
| 2005/0028812 A1 | 2/2005 | Djupesland | |
| 2005/0072430 A1 | 4/2005 | Djupesland | |
| 2005/0235992 A1 | 10/2005 | Djupesland | |
| 2006/0096589 A1 | 5/2006 | Djupesland | |
| 2006/0107957 A1 | 5/2006 | Djupesland | |
| 2006/0169278 A1 | 8/2006 | Djupesland et al. | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2007/0039614 A1 | 2/2007 | Djupesland | |
| 2007/0125371 A1 | 6/2007 | Djupesland | |
| 2007/0186927 A1 | 8/2007 | Djupesland et al. | |
| 2008/0161771 A1 | 7/2008 | Djupesland | |
| 2008/0163874 A1 | 7/2008 | Djupesland | |
| 2008/0221471 A1 | 9/2008 | Djupesland et al. | |
| 2008/0223363 A1 | 9/2008 | Djupesland | |
| 2008/0276938 A1 * | 11/2008 | Jeppesen ........... | A61M 16/0666 128/204.18 |
| 2008/0289629 A1 | 11/2008 | Djupesland et al. | |
| 2009/0101146 A1 | 4/2009 | Djupesland | |
| 2009/0293873 A1 | 12/2009 | Djupesland et al. | |
| 2009/0304802 A1 | 12/2009 | Djupesland et al. | |
| 2009/0314293 A1 | 12/2009 | Djupesland | |
| 2009/0320832 A1 | 12/2009 | Djupesland | |
| 2010/0035805 A1 | 2/2010 | Hafner | |
| 2010/0051022 A1 | 3/2010 | Djupesland et al. | |
| 2010/0057047 A1 | 3/2010 | Djupesland et al. | |
| 2010/0163042 A1 | 7/2010 | Bhowmick et al. | |
| 2010/0199984 A1 * | 8/2010 | Williams .......... | A61M 15/0065 128/200.23 |
| 2010/0242959 A1 | 9/2010 | Djupesland et al. | |
| 2010/0262033 A1 * | 10/2010 | Colman ............ | A61M 16/0488 600/532 |
| 2010/0282246 A1 | 11/2010 | Djupesland et al. | |
| 2010/0288275 A1 | 11/2010 | Djupesland et al. | |
| 2010/0300439 A1 | 12/2010 | Djupesland et al. | |
| 2011/0017304 A1 * | 1/2011 | Babl .................. | B60H 1/00564 137/1 |
| 2011/0023869 A1 | 2/2011 | Djupesland | |
| 2011/0053827 A1 | 3/2011 | Hafner | |
| 2011/0088690 A1 | 4/2011 | Djupesland et al. | |
| 2011/0088691 A1 | 4/2011 | Djupesland | |
| 2011/0114087 A1 | 5/2011 | Djupesland et al. | |
| 2011/0126830 A1 | 6/2011 | Djupesland et al. | |
| 2011/0259329 A1 | 10/2011 | Djupesland et al. | |
| 2011/0318345 A1 | 12/2011 | Djupesland | |
| 2012/0000459 A1 | 1/2012 | Djupesland | |
| 2012/0006323 A1 | 1/2012 | Djupesland | |
| 2012/0073571 A1 | 3/2012 | Djupesland | |
| 2012/0090608 A1 | 4/2012 | Djupesland et al. | |
| 2012/0260915 A1 | 10/2012 | Djupesland | |
| 2013/0098362 A1 | 4/2013 | Djupesland et al. | |
| 2013/0125889 A1 | 5/2013 | Djupesland et al. | |
| 2013/0131534 A1 * | 5/2013 | Heatherington .. | A61M 16/0666 600/532 |
| 2013/0327320 A1 | 12/2013 | Djupesland | |
| 2014/0018295 A1 | 1/2014 | Djupesland | |
| 2014/0041660 A1 | 2/2014 | Djupesland et al. | |
| 2014/0060536 A1 | 3/2014 | Djupesland | |
| 2014/0073562 A1 | 3/2014 | Djupesland | |
| 2014/0144442 A1 | 5/2014 | Djupesland et al. | |
| 2014/0144443 A1 | 5/2014 | Djupesland et al. | |
| 2014/0166008 A1 | 6/2014 | Djupesland | |
| 2014/0202456 A1 | 7/2014 | Djupesland | |
| 2014/0246022 A1 | 9/2014 | Djupesland et al. | |
| 2015/0007811 A1 | 1/2015 | Djupesland et al. | |
| 2015/0013670 A1 | 1/2015 | Djupesland et al. | |
| 2015/0013677 A1 | 1/2015 | Djupesland et al. | |
| 2015/0053201 A1 | 2/2015 | Djupesland et al. | |
| 2015/0090259 A1 | 4/2015 | Djupesland et al. | |
| 2015/0101605 A1 | 4/2015 | Djupesland et al. | |

(56) References Cited

U.S. PATENT DOCUMENTS

| | | |
|---|---|---|
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |

FOREIGN PATENT DOCUMENTS

| | | |
|---|---|---|
| GB | 2471973 | 1/2011 |
| JP | 2010/525864 | 7/2010 |
| JP | 2010/540147 | 12/2010 |
| RU | 2003128878 | 3/2005 |
| WO | WO 96/22802 | 8/1996 |
| WO | WO 98/53869 | 12/1998 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO-2008/042951 | 4/2008 |
| WO | WO 2008/065403 | 6/2008 |
| WO | WO 2008/081326 | 7/2008 |
| WO | WO 2008/081327 | 7/2008 |
| WO | WO 2008/122018 | 10/2008 |
| WO | WO 2008/122791 | 10/2008 |
| WO | WO 2008/122795 | 10/2008 |
| WO | WO-2009/008001 | 1/2009 |
| WO | WO 2009/044172 | 4/2009 |
| WO | WO 2010/029441 | 3/2010 |
| WO | WO-2010-062746 | 6/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).

Per Gisle Djupesland, *Who Nose How Far Nasal Delivery Can Go?*, EPC (Oct. 7, 2003).

Per Gisle Djupesland, *Bi-directional Nasal Drug Delivery*, Innovations in Pharmaceutical Technology (Jul. 10, 2004).

P.G. Djupesland, *Bi-Directional Nasal Delivery of Aerosols Can Prevent Lung Deposition*, Journal of Aerosol Medicine (Sep. 2004).

*Bi-Directional Nasal Device Delivers Drug on Exhalation*, Pharmaceutical Technology (Sep. 10, 2004).

Ola Dale et al., *Intranasal Midazolam: A Comparison of Two Delivery Devices in Human Volunteers*, Journal of Pharmacy and Pharmacology (Oct. 2004).

M. Kleven, *Using Computational Fluid Dynamics (CFD) to Improve the Bi-Directional Nasal Drug Delivery Concept*, Trans IChemE Part C. (Jun. 2005).

Per Gisle Djupesland, *Breath-Actuated Bi-Directional Delivery Sets the Nasal Market on a New Course*, ONdrugDelivery (Oct. 10, 2005).

Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).

P.G. Djupesland et al., *Breath Actuated Nasal Device Improves Delivery to Target Sites Beyond the Nasal Valve*, The Laryngoscope (Mar. 2006).

R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).

A. Skretting et al., *A New Method for Scintigraphic Quantification of Deposition and Clearance in Anatomical Regions of the Human Nose*, Nuclear Medicine Communications (Aug. 2009).

Vlckovia et al., *Effective Treatment of Mild-to-Moderate Nasal Polyposis with Fluticasone Delivered by a Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered by a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

Per Gisle Djupesland, *Breath Powdered Nasal Delivery: A New Route to Rapid Headache Relief*, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).

S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A*

(56) References Cited

OTHER PUBLICATIONS

*Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).

\* cited by examiner

NASAL DELIVERY DEVICES

The present invention relates to a nasal delivery device for and a method of delivering substances, in particular one of a liquid, as a suspension or solution, or a powder, containing a medicament, especially systemic or topical pharmaceuticals, or a vaccine, to the nasal airway of a subject.

Figure 7:
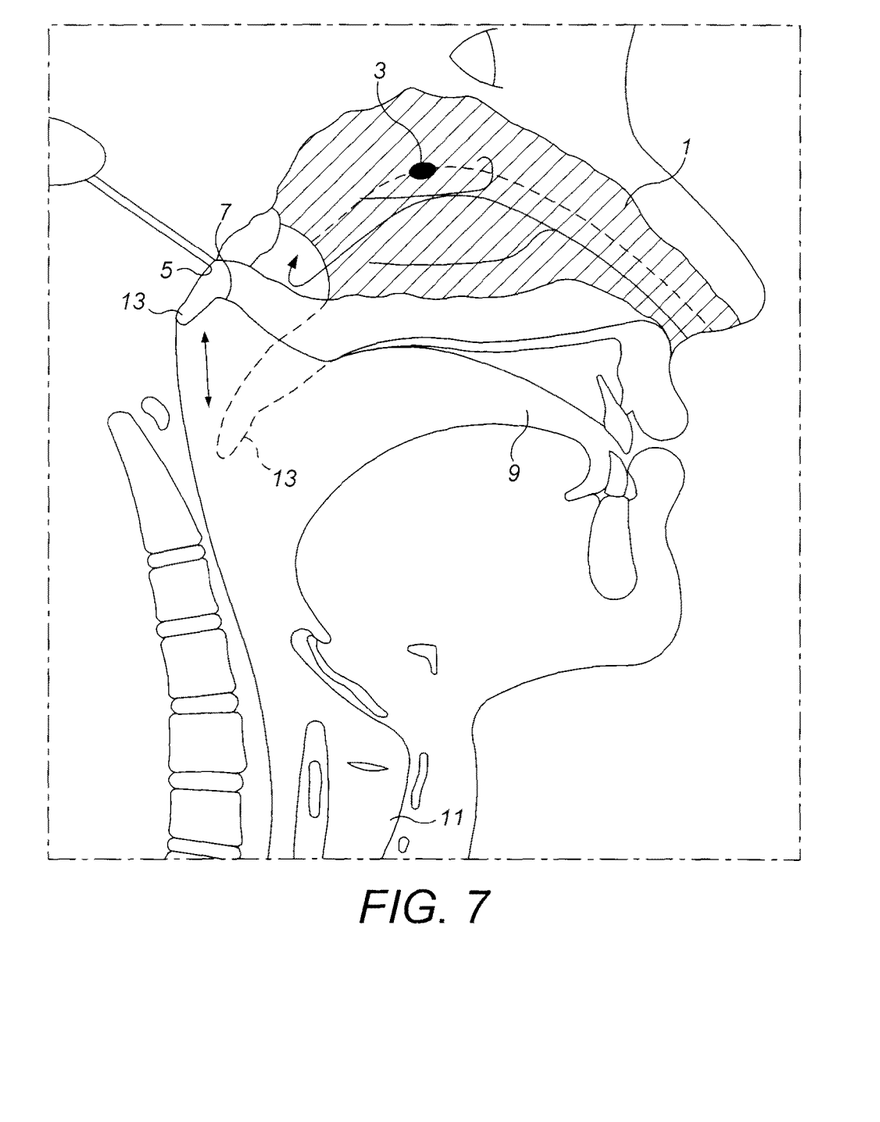
FIG. 7 schematically illustrates the anatomy of the upper respiratory tract of a human subject.

Referring to FIG. 7, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *helicobacter pylori* infections which cause gastric ulcers.

WO-A-2000/051672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide nasal delivery devices and nasal delivery methods for providing for delivery of a substance to a nasal cavity of subject, and in particular relatively-simple mechanically-actuatable delivery devices.

In one aspect the present invention provides a nasal delivery device for delivering substance to a nasal cavity of a subject, the delivery device comprising: a housing; a nosepiece for fitting to a nasal cavity of the subject; a mouthpiece through which the subject in use exhales; and a flexible coupling which couples the mouthpiece to the housing, wherein the flexible coupling provides for asymmetric translation of the mouthpiece relative to the nosepiece.

In one embodiment the nosepiece includes an outlet from which substance is delivered, and a seat against which the nare of a nostril of the subject is in use seated, in achieving a sealing fit between the nosepiece and the nasal cavity of the subject.

In one embodiment the nosepiece includes a tapered section which in use is located within a nasal cavity of the subject and tapers outwardly from the outlet.

In one embodiment the mouthpiece comprises a tubular section.

In one embodiment the tubular section is formed of a rigid material.

In one embodiment the tubular section is formed of a semi-rigid material.

In one embodiment the flexible coupling is a resilient element.

In one embodiment the asymmetric translation of the mouthpiece relative to the nosepiece provides for greater movement in a direction along the axis of the nosepiece than in a direction laterally to the nosepiece.

In one embodiment the distal end of the mouthpiece is configured to move a distance at least 1.5 times greater in a direction parallel to the axis of the nosepiece than in a direction orthogonally to the axis of the nosepiece.

In one embodiment the distal end of the mouthpiece is configured to move a distance at least 1.75 times greater in a direction parallel to the axis of the nosepiece than in a direction orthogonally to the axis of the nosepiece.

In one embodiment the distal end of the mouthpiece is configured to move a distance at least 2 times greater in a direction parallel to the axis of the nosepiece than in a direction orthogonally to the axis of the nosepiece.

In one embodiment the flexible coupling comprises an annular coupling member which is attached in one part to the housing and another part to the mouthpiece, such that exhalation through the mouthpiece delivers an air flow into the housing.

In one embodiment the coupling member is configured to provide a hinge section about which the mouthpiece is preferentially hinged when biased upwardly or downwardly by application of a biasing force.

In one embodiment the hinge section is provided to one side thereof, proximate the nosepiece.

In one embodiment the coupling member has a shorter dimension to the one side thereof, thereby ensuring that the mouthpiece is hinged about the one side of the coupling member.

In one embodiment the coupling member has a progressively-increasing dimension to the other side thereof, distal the nosepiece.

In one embodiment the coupling member has an arcuate, bowed profile which becomes larger towards the other side thereof, and provides for stretching when the mouthpiece is biased upwardly and compression when the mouthpiece is biased downwardly.

In one embodiment the profile section is bowed outwardly, whereby the biasing force required to bias the mouthpiece upwardly is less than the biasing force required to bias the mouthpiece downwardly.

In one embodiment the profile section of the coupling member is formed of graded material, such that the material of the coupling member is less resilient at the one side thereof than the other side thereof.

In one embodiment the coupling member is formed of graded material, such that the material of the coupling member is less resilient at the one side thereof than the other side thereof.

In one embodiment the coupling member is configured to provide the axis of the mouthpiece at an angle of between about 45 and about 55 degrees relative to the axis of the nosepiece.

In one embodiment the coupling member is configured to provide the axis of the mouthpiece at an angle of between about 48 and about 52 degrees relative to the axis of the nosepiece.

In one embodiment the coupling member is configured to provide the axis of the mouthpiece at an angle of about 50 degrees relative to the axis of the nosepiece.

In one embodiment the coupling member is configured to allow for the mouthpiece to be moved upwardly through an angle of between about 7 and about 17 degrees relative to the axis of the nosepiece.

In one embodiment the coupling member is configured to allow for the mouthpiece to be moved upwardly through an angle of between about 9 and about 15 degrees relative to the axis of the nosepiece.

In one embodiment the coupling member is configured to allow for the mouthpiece to be moved upwardly through an angle of between about 10 and about 14 degrees relative to the axis of the nosepiece.

In one embodiment the coupling member is configured to allow for the mouthpiece to be moved upwardly through an angle of about 12 degrees relative to the axis of the nosepiece.

In one embodiment the coupling member is configured to allow for the mouthpiece to be moved downwardly through an angle of between about 4 and about 10 degrees relative to the axis of the nosepiece.

In one embodiment the coupling member is configured to allow for the mouthpiece to be moved downwardly through an angle of between about 5 and about 9 degrees relative to the axis of the nosepiece.

In one embodiment the coupling member is configured to allow for the mouthpiece to be moved downwardly through an angle of between about 6 and about 8 degrees relative to the axis of the nosepiece.

In one embodiment the coupling member is configured to allow for the mouthpiece to be moved downwardly through an angle of about 7 degrees relative to the axis of the nosepiece.

In one embodiment the coupling member is formed of a thermoplastic elastomer (TPE).

In one embodiment the TPE has a durometer of between about 40 and about 60.

In one embodiment the TPE has a durometer of between about 45 and about 55.

In one embodiment the TPE has a durometer of about 50.

In one embodiment the delivery device further comprises: a substance supply unit which is manually actuated to deliver substance to the nasal cavity of the subject.

In another aspect the present invention provides a nasal delivery device for delivering substance to a nasal cavity of a subject, the delivery device comprising: a housing; a nosepiece for fitting to a nasal cavity of the subject; a mouthpiece through which the subject in use exhales; and a flexible coupling which couples the mouthpiece to the housing, providing for movement of the mouthpiece relative to the nosepiece.

In a further aspect the present invention provides a method of delivering substance to a nasal cavity of a subject, the method comprising the steps of: providing a nasal delivery device comprising: a housing; a nosepiece for fitting to a nasal cavity of the subject; a mouthpiece through which the subject in use exhales; and a flexible coupling which couples the mouthpiece to the housing, wherein the flexible coupling provides for asymmetric translation of the mouthpiece relative to the nosepiece; fitting the nosepiece to a nasal cavity of the subject; and locating the mouthpiece in the mouth of the subject by flexing the asymmetric coupling and thereby asymmetrically translating the mouthpiece relative to the nosepiece.

Preferred embodiments of the present invention will now be described hereinbelow by way of example only with reference to the accompanying drawings, in which.

Figure 1:
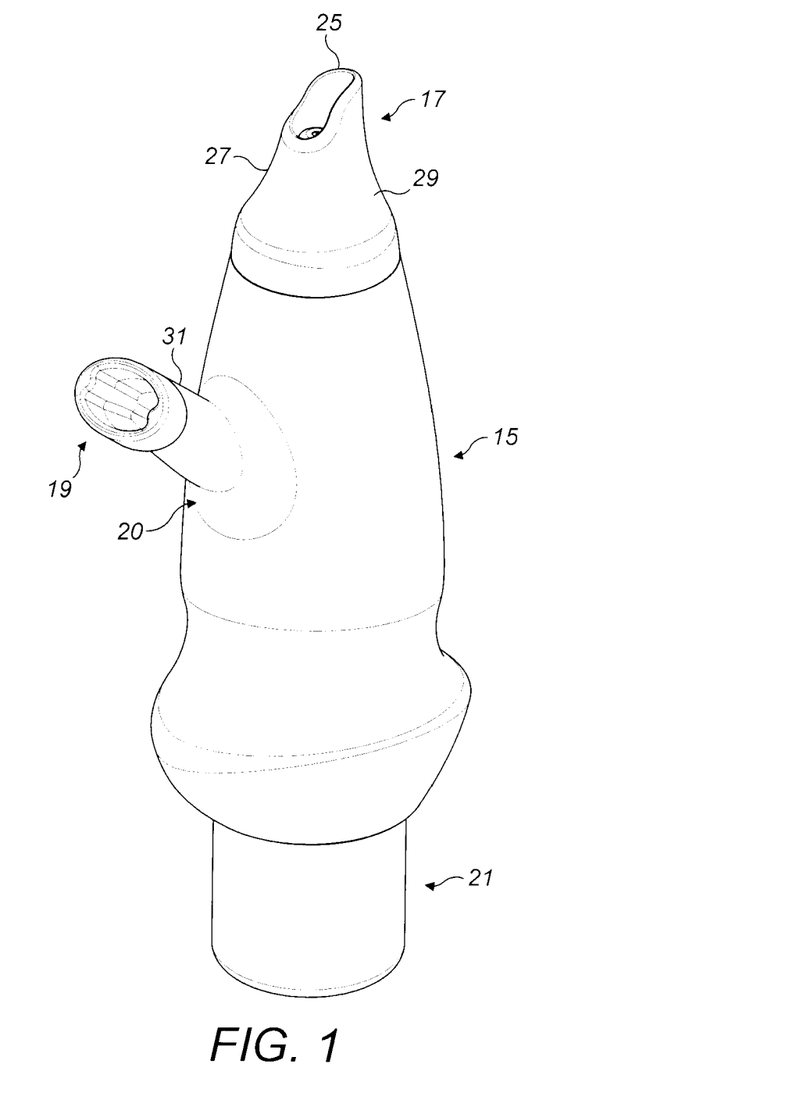
FIG. 1 illustrates a perspective view of a nasal delivery device in accordance with a first embodiment of the present invention.
Figure 2:
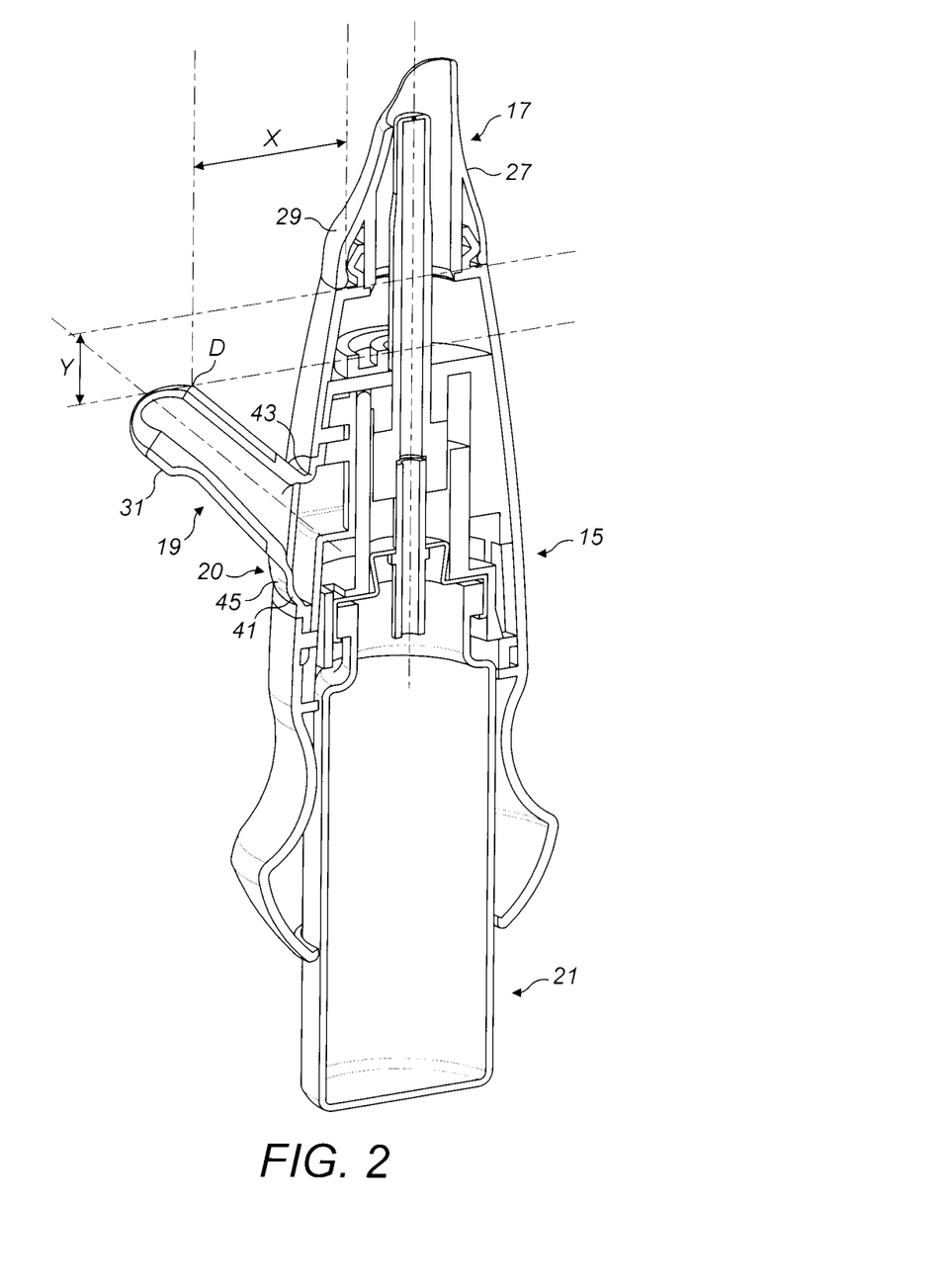
FIG. 2 illustrates a vertical sectional view of the delivery device of FIG. 1, with the mouthpiece in the at rest position.

The delivery device comprises a housing 15, a nosepiece 17 for fitting in a nasal cavity of a subject, a mouthpiece 19 through which the subject in use exhales, a flexible coupling 20 which couples the mouthpiece 19 to the housing 15, and a substance supply unit 21 which is manually actuated to deliver substance to the nasal cavity of the subject.

The nosepiece 17 includes an outlet 25 from which substance is delivered, a tapered section 27 which in use is located within a nasal cavity of the user and tapers outwardly from the outlet 25, and a seat 29 against which the nare of the nostril is in use seated, in achieving a sealing fit between the nosepiece 17 and the nasal cavity of the user.

The mouthpiece 19 comprises a tubular section 31, in this embodiment of a rigid or semi-rigid material.

The flexible coupling 20 is a resilient element which allows for movement of the mouthpiece 19 relative to the nosepiece 17, in this embodiment an asymmetric translation of the mouthpiece 19 relative to the nosepiece 17.

The present inventors have recognized that a fixed relationship between the mouthpiece 19 and the nosepiece 17 would not allow the delivery device to accommodate sufficient of the possible patient population using a single delivery device, given the variance that exists between patients, particularly in terms of age, gender and ethnicity, and have further recognized that an entirely free and flexible coupling between the mouthpiece 19 and the nosepiece 17, without any constraint, would not be sufficient, in not maintaining a desired relationship between the mouthpiece 19 and the nosepiece 17, which the present inventors have determined to be necessary to achieve a required orientation of the delivery device for optimizing delivery of substance.

The present inventors have determined that the provision of asymmetric translation of the mouthpiece 19 relative to the nosepiece 17 when the mouthpiece 19 is moved, and specifically in a manner which provides for greater movement in a direction along the axis of the nosepiece 17 than in a direction laterally to the nosepiece 17, provides an arrangement which allows for fitting of a single-sized delivery device in a much greater range of the possible patient population.

Figure 5:
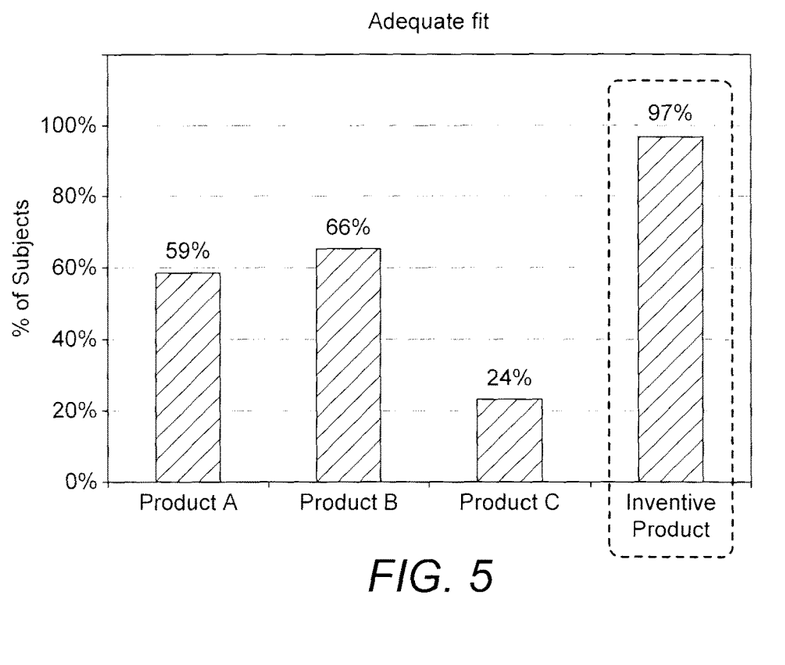
FIG. 5 illustrates the results of a study to determine adequacy of fit of the delivery device of FIG. 1, as compared to three comparator devices.

FIG. 5 illustrates the results of a study of 29 subjects to determine adequacy of fit of the delivery device, as compared to three comparator delivery devices (Products A, B and C). Adequate fit is defined as the delivery device fitting the subject and sealing sufficiently in the nose and mouth as to allow use of the delivery device, though may not find the delivery device preferable or comfortable.

In this study, the asymmetric translation of the mouthpiece 19 relative to the nosepiece 17 provides an arrangement which allowed for fitting of a single-sized delivery device in 28 of 29 subjects.

Figure 6:
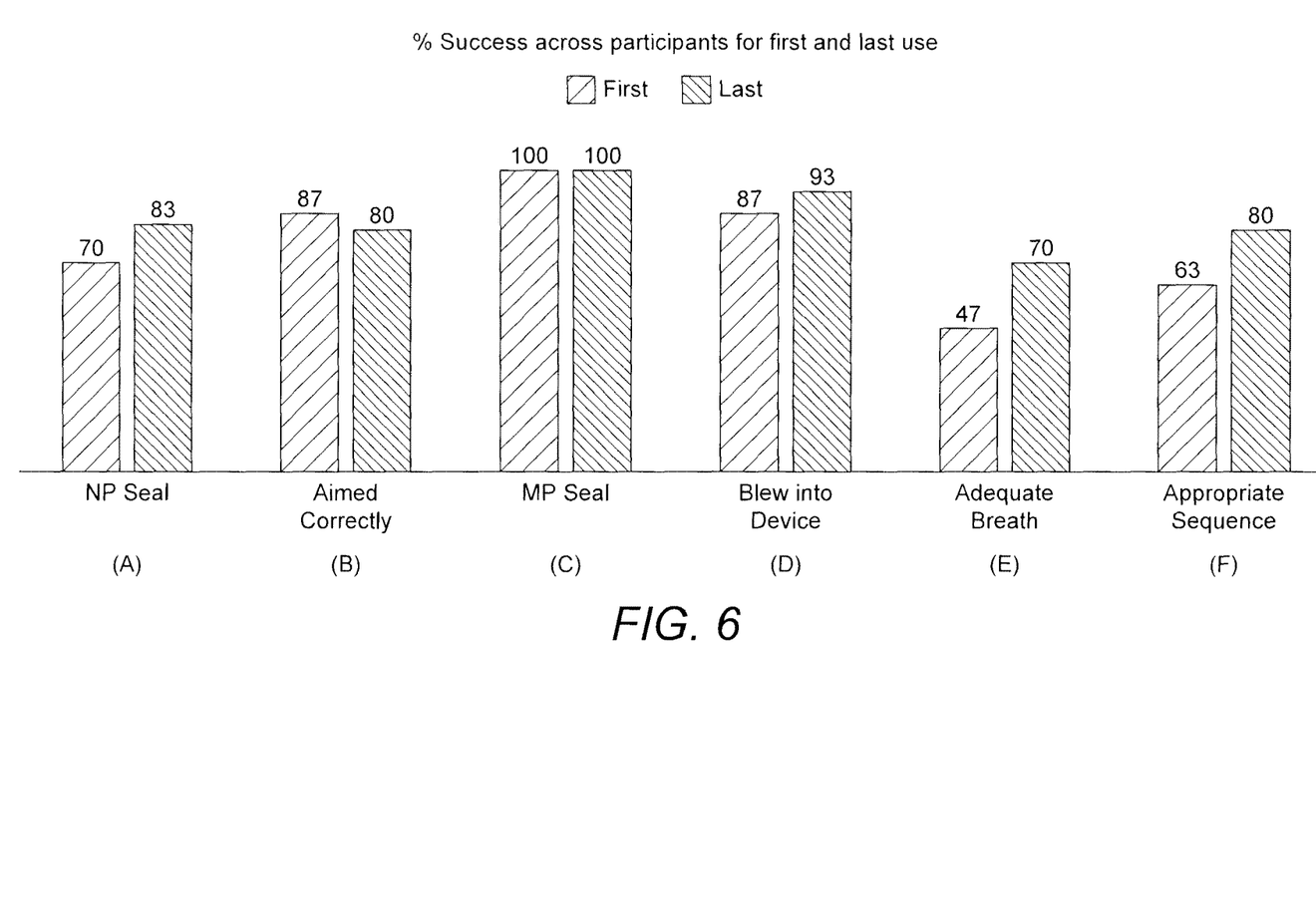
FIG. 6 illustrates success of subjects in achieving a plurality of steps in fitting the delivery device of FIG. 1.

FIG. 6 illustrates success of subjects in achieving a plurality of steps in fitting the delivery device.

In this study, the subjects were required repeatedly to perform the steps of (1) fitting the nosepiece 17 in a nasal cavity, (2) locating the mouthpiece 19 in the mouth, and (3) blowing into the mouthpiece 19.

In these steps, the following parameters were measured for the first and last sequence of steps: (A) achieving a proper seal at the nosepiece 17, (B) aiming the nosepiece 17 correctly, (C) achieving a proper seal at the mouthpiece 19, (D) blowing into the mouthpiece 19, (E) blowing into the mouthpiece 19 with adequate exhalation force, and (F) performing the sequence of steps in the appropriate order.

As will be observed, a very high degree of patient compliance is achieved by the delivery device, which improves with use of the delivery device.

Figure 3:
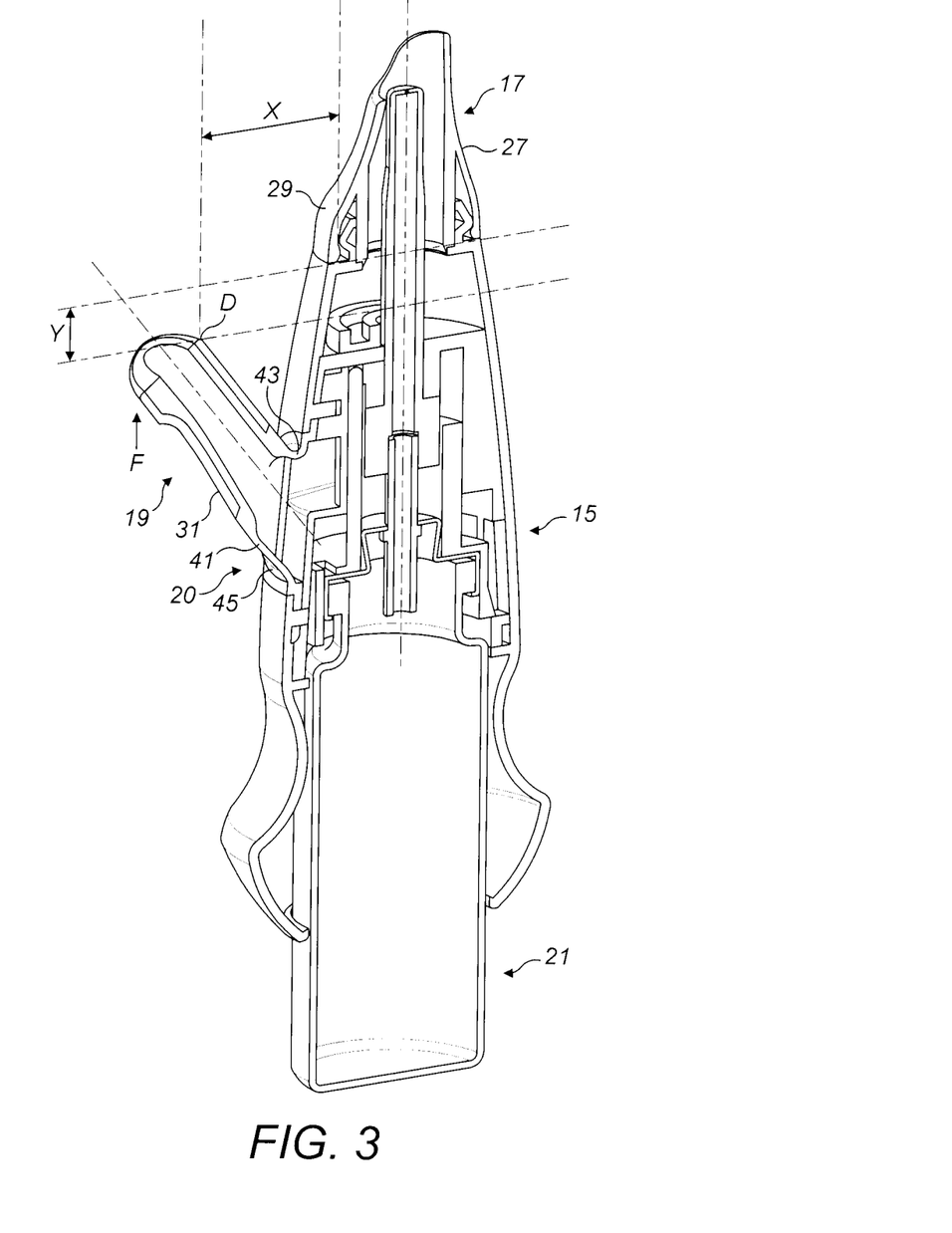
FIG. 3 illustrates a vertical sectional view of the delivery device of FIG. 1, with the mouthpiece in a position biased upwardly relative to the nosepiece.
Figure 4:
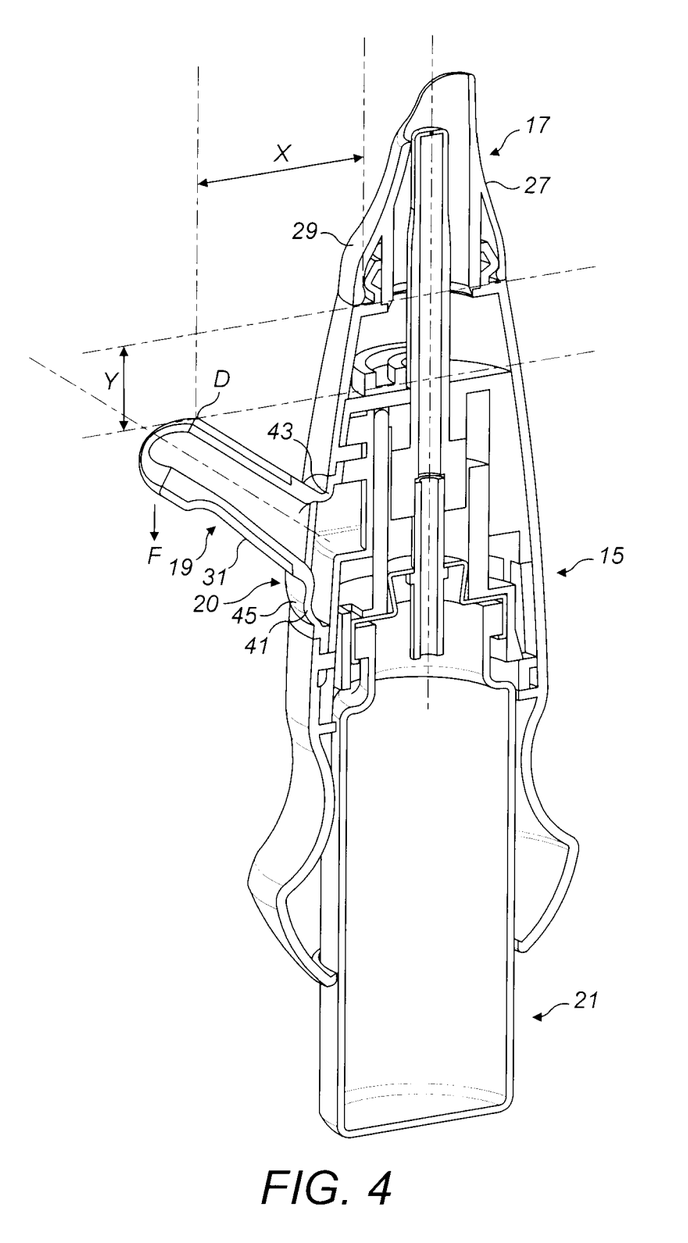
FIG. 4 illustrates a vertical sectional view of the delivery device of FIG. 1, with the mouthpiece in a position biased downwardly relative to the nosepiece.

In this embodiment the distal end D of the mouthpiece 19 is configured to move a distance Y at least 1.5 times greater in a direction parallel to the axis of the nosepiece 17 than in a direction X orthogonally to the axis of the nosepiece 17. More preferably, the distal end D of the mouthpiece 19 is configured to move a distance at least 1.75 times or at least 2 times greater in a direction Y parallel to the axis of the nosepiece 17 than in a direction X orthogonally to the axis of the nosepiece 17.

In this embodiment the flexible coupling 20 comprises an annular coupling member 41 which is attached in one part to the housing 15 and another part to the tubular section 31 of the mouthpiece 19, such that exhalation through the mouthpiece 19 delivers an air flow into the housing 15.

In this embodiment the coupling member 41 is configured to provide a hinge section 43, here, to one, upper side thereof, proximate the nosepiece 17, about which the mouthpiece 19 is preferentially hinged when biased upwardly or downwardly by the application of a biasing force F.

In this embodiment the coupling member 41 has a shorter dimension to the one, upper side, thereby ensuring that the mouthpiece 19 is hinged about the one, upper side, and a progressively-increasing dimension to the other, lower side, distal the nosepiece 17.

In this embodiment the coupling member 41 has an arcuate, bowed profile 45 which becomes larger towards the other lower side, and allows for stretching in the event of the mouthpiece 19 being biased upwardly, as illustrated in FIG. 3, and compression in the event of the mouthpiece 19 being biased downwardly, as illustrated in FIG. 4.

In this embodiment the profile section 45 is bowed outwardly, whereby the biasing force required to bias the mouthpiece 19 upwardly is less than the biasing force required to bias the mouthpiece 19 downwardly. Again, for reasons of optimizing fitting and orientation of the delivery device, the present inventors have recognized that this is achieved by requiring the mouthpiece 19 to be biased upwardly from a lower position. Thus, the delivery device is configured to facilitate operation by providing that raising the mouthpiece 19 is easier than lowering the mouthpiece 19, and this is further promoted by configuring the mouthpiece 19 such that the position of the mouthpiece 19 is lower than required for a majority of the patient population.

In this embodiment the coupling member 41 is configured to provide the axis of the mouthpiece 19 at an angle of about 50 degrees relative to the axis of the nosepiece 17, and allow for the mouthpiece 19 to be moved upwardly through an angle of about 12 degrees to enclose an angle of about 38 degrees relative to the axis of the nosepiece 17 and downwardly through an angle of about 7 degrees to enclose an angle of about 57 degrees relative to the axis of the nosepiece 17.

In an alternative embodiment the coupling member 41, instead or in addition to having a bowed profile section 45, can be formed of graded material, such that the material of the coupling member 41 is less resilient at the one, upper side than the other, lower side.

In this embodiment the coupling member 41 is formed of a thermoplastic elastomer (TPE), preferably having a durometer of 50.

Finally, it will be understood that the present invention has been described in its preferred embodiments and can be modified in many different ways without departing from the scope of the invention as defined by the appended claims.

The invention claimed is:

1. A nasal delivery device for delivering substance to a nasal cavity of a subject, the delivery device comprising:
a housing;
a nosepiece for fitting to the nasal cavity of the subject;
a mouthpiece through which the subject in use exhales, the mouthpiece having an initial untranslated position; and
a flexible coupling which couples the mouthpiece to the housing, wherein the flexible coupling is configured to constrain movement of the mouthpiece relative to the nosepiece so that, when the mouthpiece is moved in relation to the nosepiece, the mouthpiece is translated asymmetrically relative to the nosepiece, and permitted movement of the mouthpiece relative to the nosepiece is constrained to be greater in a first direction along a longitudinal axis of the nosepiece than in a second direction orthogonal to the nosepiece and facing the subject in use.

2. The delivery device of claim 1, wherein the nosepiece includes an outlet from which substance is delivered, and a seat against which the nare of a nostril of the subject is in use seated, to achieve a sealing fit between the nosepiece and the nasal cavity of the subject.

3. The delivery device of claim 2, wherein the nosepiece includes a tapered section which in use is located within the nasal cavity of the subject and tapers outwardly from the outlet toward the housing.

4. The delivery device of claim 1, wherein the mouthpiece comprises a tubular section.

5. The delivery device of claim 4, wherein the tubular section is formed of a rigid material, or a semi-rigid material.

6. The delivery device of claim 1, wherein the flexible coupling is a resilient element.

7. The delivery device of claim 1, wherein the permitted movement of the mouthpiece is at least 1.5 times greater in the first direction than in the second direction.

8. The delivery device of claim 1, wherein the permitted movement of the mouthpiece is at least 1.75 times greater in the first direction than in the second direction.

9. The delivery device of claim 1, wherein the permitted movement of the mouthpiece is at least 2 times greater in the first direction than in the second direction.

10. The delivery device of claim 1, wherein the flexible coupling comprises an annular coupling member which is attached at one end thereof to the housing and at another end thereof to the mouthpiece, such that exhalation through the mouthpiece delivers an air flow into the housing.

11. The delivery device of claim 10, wherein the annular coupling member includes a hinge section about which the mouthpiece is configured to move towards the nosepiece or away from the nosepiece by application of a biasing force.

12. The delivery device of claim 11, wherein the hinge section is provided to one side of the coupling member proximate the nosepiece.

13. The delivery device of claim 12, wherein the coupling member has a shorter dimension on the one side of the coupling member proximate the nosepiece.

14. The delivery device of claim 13, wherein the coupling member has a progressively-increasing dimension from the one side of the coupling member proximate the nosepiece to another side of the coupling member distal the nosepiece.

15. The delivery device of 10, wherein the coupling member has an arcuate, bowed profile.

16. The delivery device of claim 15, wherein the arcuate, bowed profile provides for stretching when the mouthpiece is biased towards the nosepiece and compression when the mouthpiece is biased away from the nosepiece.

17. The delivery device of claim 15, wherein the bowed profile is bowed outwardly, whereby a first biasing force required to bias the mouthpiece towards the nosepiece is less than a second biasing force required to bias the mouthpiece away from the nosepiece.

18. The delivery device of claim 15, wherein the bowed profile of the coupling member is formed of graded material, such that the material of the coupling member is less resilient at one side of the coupling member proximate the nosepiece, than another side of the coupling member distal the nosepiece.

19. The delivery device of claim 10, wherein the coupling member is formed of graded material, such that the material of the coupling member is less resilient at one side of the coupling member proximate the nosepiece, than another side of the coupling member distal the nosepiece.

20. The delivery device of claim 10, wherein an axis of the mouthpiece in the initial untranslated position is at an angle of between about 45 and about 55 degrees relative to the longitudinal axis of the nosepiece.

21. The delivery device of claim 20, wherein the axis of the mouthpiece in the initial untranslated position is at an angle of between about 48 and about 52 degrees relative to the longitudinal axis of the nosepiece.

22. The delivery device of claim 20, wherein the coupling member is configured to allow for the mouthpiece to be moved from the initial untranslated position towards the nosepiece through an angle of between about 7 and about 17 degrees relative to the longitudinal axis of the nosepiece.

23. The delivery device of claim 22, wherein the coupling member is configured to allow for the mouthpiece to be moved from the initial untranslated position towards the nosepiece through an angle of between about 9 and about 15 degrees relative to the longitudinal axis of the nosepiece.

24. The delivery device of claim 23, wherein the coupling member is configured to allow for the mouthpiece to be moved from the initial untranslated position towards the nosepiece through an angle of between about 10 and about 14 degrees relative to the longitudinal axis of the nosepiece.

25. The delivery device of claim 20, wherein the coupling member is configured to allow for the mouthpiece to be moved from the initial untranslated position away from the nosepiece through an angle of between about 4 and about 10 degrees relative to the longitudinal axis of the nosepiece.

26. The delivery device of claim 25, wherein the coupling member is configured to allow for the mouthpiece to be moved from the initial untranslated position away from the nosepiece through an angle of between about 5 and about 9 degrees relative to the longitudinal axis of the nosepiece.

27. The delivery device of claim 26, wherein the coupling member is configured to allow for the mouthpiece to be moved from the initial untranslated position away from the nosepiece through an angle of between about 6 and about 8 degrees relative to the longitudinal axis of the nosepiece.

28. The delivery device of claim 10, wherein the coupling member is formed of a thermoplastic elastomer (TPE).

29. The delivery device of claim 28, wherein the TPE has a durometer of between about 40 and about 60.

30. The delivery device of claim 29, wherein the TPE has a durometer of between about 45 and about 55.

31. The delivery device of claim 1, further comprising:
    a substance supply unit which is manually actuated to deliver substance to the nasal cavity of the subject.

32. A nasal delivery device for delivering substance to a nasal cavity of a subject, the delivery device comprising:
    a housing;
    a nosepiece for fitting to the nasal cavity of the subject;
    a mouthpiece through which the subject in use exhales, the mouthpiece having an initial untranslated position; and
    a flexible coupling configured to constrain movement of the mouthpiece relative to the nosepiece so that, when the mouthpiece is moved in relation to the nosepiece, the mouthpiece is translated asymmetrically relative to the nosepiece, and permitted movement of the mouthpiece relative to the nosepiece is constrained to be greater in a first direction along a longitudinal axis of the nosepiece than in a second direction orthogonal to the nosepiece and facing the subject in use.

33. The delivery device of claim 32, wherein the nosepiece includes an outlet from which substance is delivered, and a seat against which the nare of a nostril of the subject is in use seated, in achieving a sealing fit between the nosepiece and the nasal cavity of the subject.

34. The delivery device of claim 32, wherein the flexible coupling is a resilient element.

35. The delivery device of claim 32, wherein the permitted movement of the mouthpiece is at least 1.5 times greater in the first direction than in the second direction.

36. The delivery device of claim 32, wherein the permitted movement of the mouthpiece is at least 1.75 times greater in the first direction than in the second direction.

37. The delivery device of claim 32, wherein the permitted movement of the mouthpiece is at least 2 times greater in the first direction than in the second direction.

38. The delivery device of claim 32, wherein an axis of the mouthpiece in the initial untranslated position is at an angle of between about 45 and about 55 degrees relative to the longitudinal axis of the nosepiece.

39. The delivery device of claim 38, wherein the axis of the mouthpiece in the initial untranslated position is at an angle of between about 48 and about 52 degrees relative to the longitudinal axis of the nosepiece.

40. The delivery device of claim 38, wherein the flexible coupling is configured to allow for the mouthpiece to be moved from the initial untranslated position towards the nosepiece through an angle of between about 7 and about 17 degrees relative to the longitudinal axis of the nosepiece.

41. The delivery device of claim 40, wherein the flexible coupling is configured to allow for the mouthpiece to be moved from the initial untranslated position towards the nosepiece through an angle of between about 9 and about 15 degrees relative to the longitudinal axis of the nosepiece.

42. The delivery device of claim 41, wherein the flexible coupling is configured to allow for the mouthpiece to be moved from the initial untranslated position towards the nosepiece through an angle of between about 10 and about 14 degrees relative to the longitudinal axis of the nosepiece.

43. The delivery device of claim 42, wherein the flexible coupling is configured to allow for the mouthpiece to be moved from the initial untranslated position towards the nosepiece through an angle of about 12 degrees relative to the longitudinal axis of the nosepiece.

44. The delivery device of claim 38, wherein the flexible coupling is configured to allow for the mouthpiece to be moved from the initial untranslated position away from the nosepiece through an angle of between about 4 and about 10 degrees relative to the longitudinal axis of the nosepiece.

45. The delivery device of claim 44, wherein the flexible coupling is configured to allow for the mouthpiece to be moved from the initial untranslated position away from the nosepiece through an angle of between about 5 and about 9 degrees relative to the longitudinal axis of the nosepiece.

46. The delivery device of claim 45, wherein the flexible coupling is configured to allow for the mouthpiece to be moved from the initial untranslated position away from the nosepiece through an angle of between about 6 and about 8 degrees relative to the longitudinal axis of the nosepiece.

47. The delivery device of claim 32, further comprising:
    a substance supply unit which is manually actuated to deliver substance to the nasal cavity of the subject.

* * * * *

UNITED STATES PATENT AND TRADEMARK OFFICE
CERTIFICATE OF CORRECTION

PATENT NO. : 10,076,614 B2
APPLICATION NO. : 14/380801
DATED : September 18, 2018
INVENTOR(S) : Per Gisle Djupesland et al.

It is certified that error appears in the above-identified patent and that said Letters Patent is hereby corrected as shown below:

In the Claims

Claim 15, Column 8, Lines 26-27, "The delivery device of 10, wherein the coupling member has an arcuate, bowed profile." should read --The delivery device of claim 10, wherein the coupling member has an arcuate, bowed profile.--.

Signed and Sealed this
Thirteenth Day of November, 2018

Andrei Iancu
*Director of the United States Patent and Trademark Office*